(12) United States Patent
Defossa et al.

(10) Patent No.: US 7,078,404 B2
(45) Date of Patent: Jul. 18, 2006

(54) ACYL-3-CARBOXYPHENYLUREA DERIVATIVES, PROCESSES FOR PREPARING THEM AND THEIR USE

(75) Inventors: Elisabeth Defossa, Idstein (DE); Dieter Kadereit, Kelkheim (DE); Karl Schoenafinger, Alzenau (DE); Thomas Klabunde, Frankfurt (DE); Hans-Joerg Burger, Morristown, NJ (US); Andreas Herling, Bad Camberg (DE); Karl-Ulrich Wendt, Frankfurt (DE); Erich Von Roedern, Hattersheim (DE); Alfons Enhsen, Buttelborn (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 83 days.

(21) Appl. No.: 10/410,892

(22) Filed: Apr. 10, 2003

(65) Prior Publication Data

US 2003/0216370 A1    Nov. 20, 2003

(30) Foreign Application Priority Data

Apr. 11, 2002    (DE) ............................... 102 15 908

(51) Int. Cl.
- A61K 31/50 (2006.01)
- C07D 241/04 (2006.01)
- C07D 263/32 (2006.01)
- C07D 307/06 (2006.01)
- C07C 243/09 (2006.01)

(52) U.S. Cl. .................. 514/247; 514/247; 514/374; 514/473; 514/563; 544/392; 544/393; 548/236; 548/577; 549/295; 562/439

(58) Field of Classification Search ............... 562/439; 544/392, 393; 514/563; 548/577, 236; 549/263
See application file for complete search history.

(56) References Cited

U.S. PATENT DOCUMENTS

| 5,190,923 A | 3/1993 | Vincent et al. |
| 6,221,633 B1 | 4/2001 | Ertl |
| 6,221,897 B1 | 4/2001 | Baringhaus |
| 6,245,744 B1 | 6/2001 | Baringhaus |
| 6,342,512 B1 | 1/2002 | Kirsch |
| 6,380,230 B1 | 4/2002 | Brodin et al. |
| 6,506,778 B1 | 1/2003 | Defossa et al. |
| 2003/0144332 A1 | 7/2003 | Glombik |
| 2004/0077716 A1* | 4/2004 | Defossa et al. ............. 514/522 |
| 2004/0087659 A1* | 5/2004 | Defossa et al. ............. 514/586 |

FOREIGN PATENT DOCUMENTS

| DE | 10142734 | 3/2003 |
| EP | 0 193 249 | 9/1986 |
| EP | 0 462 884 | 6/1993 |

(Continued)

OTHER PUBLICATIONS

Asakawa A et al., Cocaine-Amphetamine-Regulated Transcript Influences Energy Metabolism, Anxiety and Gastric Emptying in Mice, Hormone and Metabolic Research, 2001, vol. 33(9), pp 554-558.

Drueckes P et al., Photometric Microliter Assay of Inorganic Phosphate in the Presence of Acid-Labile Organic Phosphates, Anal. Biochem, 1995, vol. 230(1), pp. 173-177.

Engers H D et al., Kinetic mechanism of phosphorylase a. I. Initial velocity studies, Can J. Biochem., 1970, vol. 48(7) pp 746-854.

Lee Daniel W et al., Leptin agonists as a potential approach to the treatment of obesity, Drugs of the Future, 2001, vol. 26(9), pp. 873-881.

Okada Hiroshi et al., Syntheisis and Antiutumer Activities of Prodrugs of Benzopylphenylureas, Chem. Pharm. Bull., 1994, vol. 42(1), pp. 57-61.

Salvador Javier et al. Perspectives in the terapeutic use of leptin, Expert Opinion on Pharmacotherapy. 201, vol. 2(10, pp 1615-1622, (2001).

Tyle Praveen, Iontophoretic Devices for Drug Delivery, Pharmaceutical Research, 1986, vol. 3, No. 6, pp. 318-326.

Zunft H J et al., Carob Pulp Preparation for Treatment of Hypercholesterolemia, Advances in therapy, 2001, vol. 18(5), pp. 230-236.

*Primary Examiner*—Taofiq Solola
*Assistant Examiner*—Ebenezer Sackey
(74) *Attorney, Agent, or Firm*—Barbara E. Kurys

(57) ABSTRACT

The invention relates to acyl-3-carboxyphenylurea derivatives and to their physiologically tolerated salts and physiologically functional derivatives.

The invention relates to compounds of formula I,

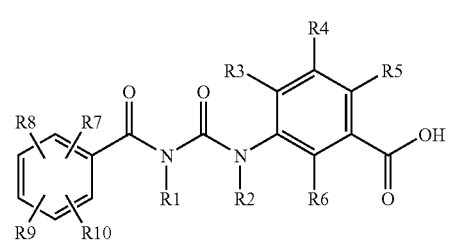

in which the radicals have the given meanings, and to their physiologically tolerated salts and processes for preparing them. The compounds are, for example, suitable for use as antidiabetics.

10 Claims, No Drawings

FOREIGN PATENT DOCUMENTS

| | | |
|---|---|---|
| WO | WO 97/26265 | 7/1997 |
| WO | WO 97/41097 | 11/1997 |
| WO | WO 96/08871 | 3/1998 |
| WO | WO 99/03861 | 1/1999 |
| WO | WO 99/15525 | 4/1999 |
| WO | WO 00/40569 | 7/2000 |
| WO | WO 00/83208 | 10/2000 |
| WO | WO00/64876 | 11/2000 |
| WO | WO00/64888 | 11/2000 |
| WO | WO 00/66585 | 11/2000 |
| WO | WO 00/71549 A1 | 11/2000 |
| WO | WO 00/78312 A1 | 12/2000 |
| WO | WO 01/09111 A1 | 2/2001 |
| WO | WO 01/83451 A1 | 11/2001 |
| WO | WO 01/85695 A1 | 11/2001 |
| WO | WO 01/91752 A1 | 12/2001 |
| WO | WO 01/94300 | 12/2001 |

* cited by examiner

ACYL-3-CARBOXYPHENYLUREA DERIVATIVES, PROCESSES FOR PREPARING THEM AND THEIR USE

The invention relates to acyl-3-carboxyphenylurea derivatives and to their physiologically tolerated salts and physiologically functional derivatives.

EP 0 193 249 (Duphar) describes acylcarboxyphenylurea derivatives which possess antitumor activity.

The invention was based on the object of providing compounds which can be used for preventing and treating diabetes type 2. In particular, the object was to make available novel compounds which have an effect which is markedly superior to that of the compounds disclosed in EP 0 193 249.

The invention therefore relates to compounds of the formula I,

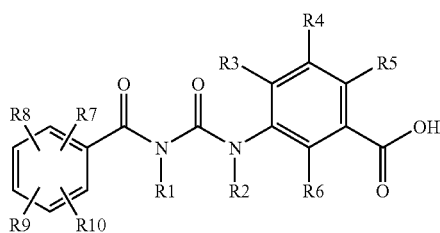

in which

R7, R8, R9 and R10 are, independent of each other, H, F, Cl, Br, OH, $NO_2$, CN, O—$(C_1$–$C_6)$-alkyl, O—$(C_2$–$C_6)$-alkenyl, O—$(C_2$–$C_6)$-alkynyl, O—$SO_2$—$(C_1$–$C_4)$-alkyl, $(C_1$–$C_6)$-alkyl, $(C_2$–$C_6)$-alkenyl or $(C_2$–$C_6)$—alkynyl, where alkyl, alkenyl and alkynyl can be substituted, once or more than once, by F, Cl or Br;

R1 and R2 are, independent of each other, H, $(C_1$–$C_6)$-alkyl, where alkyl can be substituted by OH, O—$(C_1$–$C_4)$-alkyl, $NH_2$, NH$(C_1$–$C_4)$—alkyl or N[$(C_1$–$C_6)$-alkyl]$_2$, O—$(C_1$–$C_6)$-alkyl, CO—$(C_1$–$C_6)$-alkyl, COO—$(C_1$–$C_6)$-alkyl, $(C_1$–$C_6)$-alkylene-COOH or $(C_1$–$C_6)$—alkylene-COO—$(C_1$–$C_6)$-alkyl;

R3 is H, F, Cl, Br, $NO_2$, CN, O—R11, O-phenyl, S—R11, COOR11, N(R12)(R13), $(C_1$–$C_6)$-alkyl, $(C_2$–$C_6)$-alkenyl, $(C_2$–$C_6)$-alkynyl, $(C_3$–$C_7)$-cycloalkyl or $(C_3$–$C_7)$-cycloalkyl-$(C_1$–$C_4)$-alkylene, where alkyl, cycloalkyl and alkynyl can be substituted, once or more than once, by F, Cl, Br, OR11, COOR11 or N(R16)(R17);

R4 is H, F, Cl, Br, $NO_2$, CN, O—R11, O-phenyl, S—R11, COOR11, N(R12)(R13), $(C_1$–$C_6)$-alkyl, $(C_2$–$C_6)$-alkenyl, $(C_2$–$C_6)$-alkynyl, $(C_3$–$C_7)$-cycloalkyl or $(C_3$–$C_7)$-cycloalkyl-$(C_1$–$C_4)$-alkylene, where alkyl, cycloalkyl and alkynyl can be substituted, once or more than once, by F, Cl, Br, OR11, COOR11 or N(R16)(R17);

R5 is H, F, Cl, Br, $NO_2$, CN, O—R11, O-phenyl, S—R11, COOR11, N(R12)(R13), $(C_1$–$C_6)$-alkyl, $(C_2$–$C_6)$-alkenyl, $(C_2$–$C_6)$-alkynyl, $(C_3$–$C_7)$-cycloalkyl or $(C_3$–$C_7)$-cycloalkyl-$(C_1$–$C_4)$-alkylene, where alkyl, cycloalkyl and alkynyl can be substituted, once or more than once, by F, Cl, Br, OR11, COOR11 or N(R16)(R17);

R6 is H, F, Cl, Br, $NO_2$, CN, O—R11, O-phenyl, S—R11, COOR11, N(R12)(R13), $(C_1$–$C_6)$-alkyl, $(C_2$–$C_6)$-alkenyl, $(C_2$–$C_6)$-alkynyl, $(C_3$–$C_7)$-cycloalkyl or $(C_3$–$C_7)$-cycloalkyl-$(C_1$–$C_4)$-alkylene, where alkyl, cycloalkyl and alkynyl can be substituted, once or more than once, by F, Cl, Br, OR11, COOR11 or N(R16)(R17);

R11 is H, $(C_1$–$C_8)$-alkyl, $(C_2$–$C_8)$-alkenyl or $(C_2$–$C_8)$-alkynyl, where alkyl, alkenyl and alkynyl can be substituted, once or more than once, by F, Cl, Br, OH or O—$(C_1$–$C_4)$-alkyl;

R12 and R13 are, independent of each other, H, $(C_1$–$C_8)$-alkyl, $(C_2$–$C_8)$—alkenyl, $(C_2$–$C_8)$-alkynyl, $(C_3$–$C_7)$-cycloalkyl, $(C_3$–$C_7)$-cycloalkyl-$(C_1$–$C_4)$-alkylene, COO—$(C_1$–$C_4)$-alkyl, COO—$(C_2$–$C_4)$-alkenyl, phenyl or $SO_2$-phenyl, where the phenyl ring can be substituted, up to two times, by F, Cl, CN, OH, $(C_1$–$C_6)$-alkyl, O—$(C_1$–$C_6)$-alkyl, $CF_3$, $OCF_3$, COOH, COO—$(C_1$–$C_6)$-alkyl or $CONH_2$;

or R12 and R13 form, together with the nitrogen atom to which they are bonded, a 3–7-membered, saturated heterocyclic ring which can contain up to 2 further heteroatoms from the group N, O or S and where the heterocyclic ring can be substituted, up to four times, by F, Cl, Br, OH, Oxo, $(C_1$–$C_4)$-alkyl or N(R14)(R15);

R14 and R15 are, independent of each other, H, $(C_1$–$C_8)$-alkyl, $(C_2$–$C_8)$—alkenyl, $(C_2$–$C_8)$-alkynyl, $(C_3$–$C_7)$-cycloalkyl, $(C_3$–$C_7)$-cycloalkyl-$(C_1$–$C_4)$-alkylene, COO—$(C_1$–$C_4)$-alkyl, COO—$(C_2$–$C_4)$-alkenyl, phenyl or $SO_2$-phenyl, where the phenyl ring can be substituted, up to two times, by F, Cl, CN, OH, $(C_1$–$C_6)$-alkyl, O—$(C_1$–$C_6)$-alkyl, $CF_3$, $OCF_3$, COOH, COO$(C_1$–$C_6)$-alkyl or $CONH_2$;

R16 and R17 are, independent of each other, H, $(C_1$–$C_8)$-alkyl, $(C_2$–$C_8)$—alkenyl, $(C_2$–$C_8)$-alkynyl, $(C_3$–$C_7)$-cycloalkyl, $(C_3$–$C_7)$-cycloalkyl-$(C_1$–$C_4)$-alkylene, COO—$(C_1$–$C_4)$-alkyl, COO—$(C_2$–$C_4)$-alkenyl, phenyl or $SO_2$-phenyl, where the phenyl ring can be substituted, up to two times, by F, Cl, CN, OH, $(C_1$–$C_6)$-alkyl, O—$(C_1$–$C_6)$-alkyl, $CF_3$, $OCF_3$, COOH, COO—$(C_1$–$C_6)$-alkyl or $CONH_2$;

or R16 and R17 form, together with the nitrogen atom to which they are bonded, a 3–7-membered, saturated heterocyclic ring which can contain up to 2 further heteroatoms from the group N, O or S and where the heterocyclic ring can be substituted, up to four times, by F, Cl, Br, OH, Oxo, $(C_1$–$C_4)$-alkyl or N(R14)(R15);

and the physiologically tolerated salts thereof.

Preference is given to compounds of the formula I in which one or more radicals have the following meaning:

R7, R8, R9 and R10 are, independent of each other, H, F, Cl, Br, OH, $NO_2$, CN, $(C_1$–$C_6)$-alkyl or O—$(C_1$–$C_6)$-alkyl;

R1 and R2 are H;

R3 is H, F, Cl, Br, $NO_2$, CN, O—R11, O-phenyl, S—R11, COOR11, N(R12)(R13), $(C_1$–$C_6)$-alkyl, $(C_2$–$C_6)$-alkenyl, $(C_2$–$C_6)$-alkynyl, $(C_3$–$C_7)$-cycloalkyl or $(C_3$–$C_7)$-cycloalkyl-$(C_1$–$C_4)$-alkylene, where alkyl, cycloalkyl and alkynyl can be substituted, once or more than once, by F, Cl, Br, OR11, COOR11 or N(R16)(R17);

R4 is H, F, Cl, Br, $NO_2$, CN, O—R11, O-phenyl, S—R11, COOR11, N(R12)(R13), $(C_1$–$C_6)$-alkyl, $(C_2$–$C_6)$-alkenyl, $(C_2$–$C_6)$-alkynyl, $(C_3$–$C_7)$-cycloalkyl or $(C_3$–$C_7)$-cycloalkyl-$(C_1$–$C_4)$-alkylene, where alkyl, cycloalkyl and alkynyl can be substituted, once or more than once, by F, Cl, Br, OR11, COOR11 or N(R16)(R17);

R5 is H, F, Cl, Br, $NO_2$, CN, O—R11, O-phenyl, S—R11, COOR11, N(R12)(R13), $(C_1$–$C_6)$-alkyl, $(C_2$–$C_6)$-alkenyl, $(C_2$–$C_6)$-alkynyl, $(C_3$–$C_7)$-cycloalkyl or $(C_3$–$C_7)$-cycloalkyl-$(C_1$–$C_4)$-alkylene, where alkyl, cycloalkyl and alkynyl can be substituted, once or more than once, by F, Cl, Br, OR11, COOR11 or N(R16)(R17);

R6 is H, F, Cl, Br, $NO_2$, CN, O—R11, O-phenyl, S—R11, COOR11, N(R12)(R13), ($C_1$–$C_6$)-alkyl, ($C_2$–$C_6$)-alkenyl, ($C_2$–$C_6$)-alkynyl, ($C_3$–$C_7$)-cycloalkyl or ($C_3$–$C_7$)-cycloalkyl-($C_1$–$C_4$)-alkylene, where alkyl, cycloalkyl and alkynyl can be substituted, once or more than once, by F, Cl, Br, OR11, COOR11 or N(R16)(R17);

R11 is H, ($C_1$–$C_8$)-alkyl, ($C_1$–$C_8$)-alkylene-O—($C_1$–$C_8$)-alkyl or ($C_1$–$C_8$)-alkyl-OH, where alkyl can be substituted, once or more than once, by F;

R12 and R13 are, independent of each other, H or ($C_1$–$C_8$)-alkyl;

R14 and R15 are, independent of each other, H, ($C_1$–$C_8$)-alkyl, ($C_2$–$C_8$)—alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, where the phenyl ring can be substituted, up to two times, by F, Cl, CN, OH, ($C_1$–$C_6$)-alkyl, O—($C_1$–$C_6$)-alkyl, $CF_3$, $OCF_3$, COOH, COO($C_1$–$C_6$)-alkyl or $CONH_2$;

R16 and R17 are, independent of each other, H, ($C_1$–$C_8$)-alkyl, ($C_2$–$C_8$)—alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, where the phenyl ring can be substituted, up to two times, by F, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or R16 and R17 form, together with the nitrogen atom to which they are bonded, a 3–7-membered, saturated heterocyclic ring which can contain up to 2 further heteroatoms from the group N, O or S and where the heterocyclic ring can be substituted, up to four times, by F, Cl, Br, OH, Oxo, ($C_1$–$C_4$)-alkyl or N(R14)(R15);

and the physiologically tolerated salts thereof.

Very particular preference is given to compounds of the formula I in which one or more radicals have the following meaning:

R7, R8, R9 and R10 are, independent of each other, H, F, Cl or $CH_3$;

R1, R2, R4, R5 and R6 are H;

R3 is F, Cl, $CF_3$, O—R11 or O-phenyl;

R11 is H, ($C_1$–$C_8$)-alkyl, ($C_1$–$C_8$)-alkylene-O—($C_1$–$C_8$)-alkyl or ($C_1$–$C_8$)-alkyl-OH;

and the physiologically tolerated salts thereof.

If radicals or substituents can occur more than once in the compounds of the formula I, such as —O—R11, they can then all, independent of each other, have the given meanings and be identical or different.

The invention relates to compounds of the formula I, in the form of their racemates, racemic mixtures and pure enantiomers, and to their diastereomers and mixtures thereof.

The alkyl radicals in the substituents R1, R2, R3, R4, R5, R6, R7, R8, R9, R10, R11, R12, R13, R14, R15, R16 and R17 can be either straight-chain or branched.

Because of their higher solubility in water as compared with the starting compounds or basal compounds, pharmaceutically tolerated salts are particularly suitable for medical applications. These salts must possess a pharmaceutically tolerated anion or cation. Suitable pharmaceutically tolerated acid addition salts of the compounds according to the invention are salts of inorganic acids, such as hydrochloric acid, hydrobromic acid, phosphoric acid, metaphosphoric acid, nitric acid and sulfuric acid, and also of organic acids, such as acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically tolerated basic salts are ammonium salts, alkali metal salts (such as sodium salts and potassium salts), alkaline earth metal salts (such as magnesium salts and calcium salts), trometamol (2-amino-2-hydroxymethyl-1,3-propanediol), diethanolamine, lysine or ethylenediamine.

Salts which contain an anion which is not pharmaceutically tolerated, such as trifluoroacetate, also belong within the scope of the invention as useful intermediates for preparing or purifying pharmaceutically tolerated salts and/or for use in nontherapeutic, for example in-vitro, applications.

The term "physiologically functional derivative" which is used here denotes any physiologically tolerated derivative of a compound according to the invention of the formula I, e.g. an ester which is able, on being administered to a mammal, such as a human, to form (directly or indirectly) a compound of the formula I or an active metabolite thereof.

The physiologically functional derivatives also include prodrugs of the compounds according to the invention, as described, for example, in H.

Okada et al., Chem. Pharm. Bull, 1994, 42, 57–61. Such prodrugs can be metabolized in vivo to give a compound according to the invention. These prodrugs may or may not themselves be active.

The compounds according to the invention can also be present in different polymorphic forms, e.g. as amorphous and crystalline polymorphous forms. All polymorphous forms of the compounds according to the invention belong within the scope of the invention and are another aspect of the invention.

In that which follows, all references to "compound(s) according to formula I" refer to compound(s) of the formula I as described above and to their salts, solvates and physiologically functional derivatives as described herein.

The compound(s) of the formula (I) can also be administered in combination with other active compounds.

The quantity of a compound according to Formula I which is required in order to achieve the desired biological effect depends on a number of factors, e.g. the specific compound which is selected, the intended use, the nature of administration and the clinical condition of the patient. In general, the daily dose is in the range from 0.3 mg to 100 mg (typically from 3 mg and 50 mg) per day per kilogram of bodyweight, e.g. 3–10 mg/kg/day. An intravenous dose can, for example, be in the range from 0.3 mg to 1.0 mg/kg, which dose can expediently be administered as an infusion of from 10 ng to 100 ng per kilogram per minute. Infusion solutions which are suitable for these purposes can, for example, contain from 0.1 ng to 10 mg, typically from 1 ng to 10 mg, per milliliter. Individual doses can, for example, contain from 1 mg to 10 g of the active compound. Thus, ampoules for injections can, for example, contain from 1 mg to 100 mg, and orally administrable individual dose formulations, such as tablets or capsules, can, for example, contain from 1.0 to 1000 mg, typically from 10 to 600 mg. While, for the therapy of the abovementioned conditions, the compounds according to formula I can be used themselves as compounds, they are preferably present, together with a tolerated excipient, in the form of a pharmaceutical composition. The excipient naturally has to be tolerated in the sense that it is compatibie with the other components of the composition and is not harmful to the health of the patient. The excipient can be a solid or a liquid or both and is preferably formulated together with the compound as an individual dose, for example as a tablet, which can contain from 0.05% to 95% by weight of the active compound. Other pharmaceutically active substances can also be present, including other compounds according to formula I. The pharmaceutical compositions according to the invention can be prepared using one of the known pharmaceutical methods, which essentially consist in the constituents being mixed with pharmacologically tolerated excipients and/or auxiliary substances.

Pharmaceutical compositions according to the invention are those which are suitable for oral, rectal, topical, peroral (e.g. sublingual) and parenteral (e.g. subcutaneous, intramuscular, intradermal or intravenous) administration, even though the most suitable mode of administration depends, in each individual case, on the nature and severity of the condition to be treated and on the nature of the compound according to formula I which is employed in each case. Coated formulations and coated delayed-release formulations also belong within the scope of the invention. Preference is given to formulations which are acid-resistant and gastric juice-resistant. Suitable gastric juice-resistant coatings include cellulose acetate phthalate, polyvinyl acetate phthalate, hydroxypropylmethyl cellulose phthalate and anionic polymers of methacrylic acid and methyl methacrylate.

Suitable pharmaceutical compounds for oral administration can be present in separate units, such as capsules, cachets, sucking tablets or tablets which in each case contain a defined quantity of the compound according to formula I; as powders or granules; as a solution or suspension in an aqueous or nonaqueous liquid; or as an oil-in-water or water-in-oil emulsion. As already mentioned, these compositions can be prepared using any suitable pharmaceutical method which comprises a step in which the active compound and the excipient (which can be composed of one or more additional constituents) are brought into contact. In general, the compositions are prepared by uniformly and homogeneously mixing the active compound with a liquid and/or finely divided solid excipient, after which the product is molded, if required. Thus, a tablet, for example, can be prepared by pressing or molding a powder or granulate of the compound, where appropriate together with one or more additional constituents. Pressed tablets can be prepared by tableting the compound in freely flowing form, such as a powder or granulate, where appropriate mixed with a binding agent, lubricant, inert diluent and/or a (several) surface-active/dispersing agent(s) in a suitable machine. Molded tablets can be prepared by molding the pulverulent compound, which is moistened with an inert liquid diluent, in a suitable machine.

Pharmaceutical compositions which are suitable for peroral (sublingual) administration include sucking tablets, which contain a compound according to formula I together with a flavoring agent, usually sucrose and gum arabic or tragacanth, and lozenges, which comprise the compound in an inert base such as gelatin and glycerol or sucrose and gum arabic.

Suitable pharmaceutical compositions for parenteral administration preferably include sterile aqueous preparations of a compound according to formula I which are preferably isotonic with the blood of the intended recipient. These preparations are preferably administered intravenously, even though the administration can also take place as an injection subcutaneously, intramuscularly or intradermally. These preparations can preferably be prepared by mixing the compound with water and making the resulting solution sterile and isotonic with the blood. In general, injectable compositions according to the invention comprise from 0.1 to 5% by weight of the active compound.

Suitable pharmaceutical compositions for rectal administration are preferably present as individual dose suppositories. These can be prepared by mixing a compound according to formula I with one or more conventional solid excipients, for example cocoa butter, and molding the resulting mixture.

Suitable pharmaceutical compositions for topical use on the skin are preferably present as an ointment, cream, lotion, paste, spray, aerosol or oil. Excipients which can be used are vaseline, lanolin, polyethylene glycols, alcohols and combinations of two or more of these substances. The active compound is generally present at a concentration of from 0.1 to 15% by weight of the composition, for example from 0.5 to 2%.

Transdermal administration is also possible. Suitable pharmaceutical compositions for transdermal uses can be present as individual plasters which are suitable for long-term intimate contact with the epidermis of the patient. Such plasters expediently contain the active compound in an aqueous solution, which is, where appropriate, buffered, dissolved and/or dispersed in an adhesive or dispersed in a polymer. A suitable active compound concentration is from approx. 1% to 35%, preferably from approx. 3% to 15%. As a particular possibility, the active compound can, as described, for example, in Pharmaceutical Research, 2(6): 318 (1986), be released by means of electrotransport or iontophoresis.

The following are suitable for use as additional active compounds for the combination preparations:

All antidiabetics which are named in the Roten Liste [Red List] 2001, Chapter 12. They can be combined with the compounds according to the invention of the formula I, particularly for improving the effect synergistically. The active compound combination can be administered either by administering the active compounds separately to the patient or in the form of combination preparations in which several active compounds are present in one pharmaceutical preparation. Most of the active compounds which are listed below are disclosed in USP Dictionary of USAN and International Drug Names, U.S. Pharmacopeia, Rockville 2001.

Antidiabetics include insulin and insulin derivatives, such as Lantus® (see www.lantus.com) or HMR 1964, rapidly acting insulins (see U.S. Pat. No. 6,221,633), GLP-1 derivatives, such as those which were disclosed in WO 98/08871 by Novo Nordisk A/S, and hypoglycemic active compounds which are effective orally.

The hypoglycemic active compounds which are effective orally preferably include sulfonylureas, biguanidines, meglitinides, oxadiazolidinediones, thiazolidinediones, glucosidase inhibitors, glucagon antagonists, GLP-1 agonists, calcium channel openers, such as those which were disclosed by Novo Nordisk A/S in WO 97/26265 and WO 99/03861, insulin sensitizers, inhibitors of liver enzymes which are involved in stimulating gluconeogenesis and/or glycogenolysis, modulators of glucose uptake, compounds, such as antihyperlipidemic active compounds and antilipidemic active compounds, which alter fat metabolism, compounds which decrease the intake of foodstuffs, agonists of PPAR and PXR, and active compounds which act on the ATP-dependent potassium channel of the beta cells.

In one embodiment of the invention, the compounds of the formula I are administered in combination with an HMGCoA reductase inhibitor, such as simvastatin, fluvastatin, pravastatin, lovastatin, atorvastatin, cerivastatin or rosuvastatin.

In one embodiment of the invention, the compounds of the formula I are administered in combination with a cholesterol absorption inhibitor, such as ezetimibe, tiqueside or pamaqueside.

In one embodiment of the invention, the compounds of the formula I are administered in combination with a PPAR gamma agonist, such as rosiglitazone, pioglitazone, JTT-501 or GI 262570.

In one embodiment of the invention, the compounds of the formula I are administered in combination with a PPAR alpha agonist, such as GW 9578 or GW 7647.

In one embodiment of the invention, the compounds of the formula I are administered in combination with a mixed PPAR alpha/gamma agonist, such as GW 1536, AVE 8042, AVE 8134 or AVE 0847, or as described in PCT/US 11833, PCT/US 11490 or DE10142734.4.

In one embodiment of the invention, the compounds of the formula I are administered in combination with a fibrate, such as fenofibrate, clofibrate or bezafibrate.

In one embodiment of the invention, the compounds of the formula I are administered in combination with an MTP inhibitor, such as implitapide, BMS-201038 or R-103757.

In one embodiment of the invention, the compounds of the formula I are administered in combination with bile acid absorption inhibitor (see, for example, U.S. Pat. No. 6,245,744 or U.S. Pat. No. 6,221,897), such as HMR 1741.

In one embodiment of the invention, the compounds of the formula I are administered in combination with a CETP inhibitor, such as JTT-705.

In one embodiment of the invention, the compounds of the formula I are administered in combination with a polymeric bile acid adsorber, such as cholestyramine or colesevelam.

In one embodiment of the invention, the compounds of the formula I are administered in combination with an LDL receptor inducer (see U.S. Pat. No. 6,342,512), such as HMR1171 or HMR1586.

In one embodiment of the invention, the compounds of the formula I are administered in combination with an ACAT inhibitor, such as avasimibe.

In one embodiment of the invention, the compounds of the formula I are administered in combination with an antioxidant, such as OPC-14117.

In one embodiment of the invention, the compounds of the formula I are administered in combination with a lipoprotein lipase inhibitor, such as NO-1886.

In one embodiment of the invention, the compounds of the formula I are administered in combination with an ATP citrate lyase inhibitor, such as SB-204990.

In one embodiment of the invention, the compounds of the formula I are administered in combination with a squalene synthetase inhibitor, such as BMS-188494.

In one embodiment of the invention, the compounds of the formula I are administered in combination with a lipoprotein(a) antagonist, such as CI-1027 or nicotinic acid.

In one embodiment of the invention, the compounds of the formula I are administered in combination with a lipase inhibitor, such as orlistat.

In one embodiment of the invention, the compounds of the formula I are administered in combination with insulin.

In one embodiment, the compounds of the formula I are administered in combination with a sulfonylurea, such as tolbutamide, glibenclamide, glipizide or glimepiride.

In one embodiment, the compounds of the formula I are administered in combination with a biguanide, such as metformin.

In yet another embodiment, the compounds of the formula I are administered in combination with a meglitinide, such as repaglinide.

In one embodiment, the compounds of the formula I are administered in combination with a thiazolidinedione, such as troglitazone, ciglitazone, pioglitazone, rosiglitazone or the compounds which are disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as miglitol or acarbose.

In one embodiment, the compounds of the formula I are administered in combination with an active compound which acts on the ATP-dependent potassium channel of the beta cells, such as tolbutamide, glibenclamide, glipizide, glimepiride or repaglinide.

In one embodiment, the compounds of the formula I are administered in combination with more than one of the abovementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In another embodiment, the compounds of the formula I are administered in combination with CART modulators (see "Cocaine-amphetamine-regulated transcript influences energy metabolism, anxiety and gastric emptying in mice" Asakawa, A, et al., M.:Hormone and Metabolic Research (2001), 33(9), 554–558), NPY antagonists, e.g. naphthalene-1-sulfonic acid {4-[(4-aminoquinazolin-2-ylamino)methyl] cyclohexylmethyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea]; hydrochlorides (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3-agonists (e.g. 1-(4-chloro-3-methanesulfonylmethylphenyl)-2-[2-(2,3-dimethyl-1H-indol-6-yloxy)ethylamino]ethanol; hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramines), mixed serotonin compounds and noradrenergic compounds (e.g. WO 00/71549), 5HT agonists, e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (tert-butyl 6-benzyloxy-1-(2-diisopropylaminoethylcarbamoyl)-3,4-dihydro-1H-isoquinoline-2-carboxylate (WO 01/85695)), TRH agonists (see, for example, EP 0 462 884) uncoupling protein 2- or 3-modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (bromocriptine, doprexin), lipase/amylase inhibitors (e.g. WO 00/40569), PPAR modulators (e.g. WO 00/78312), RXR modulators or TR β-agonists.

In one embodiment of the invention, the additional active compound is leptin; see, e.g., "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In one embodiment, the additional active compound is dexamphetamine or amphetamine.

In one embodiment, the additional active compound is flenfluramine or dexfenfluramine.

In yet another embodiment, the additional active compound is sibutramine.

In one embodiment, the additional active compound is orlistat.

In one embodiment, the additional active compound is mazindol or phentermine.

In one embodiment, the compounds of the formula I are administered in combination with bulk materials, preferably insoluble bulk materials (see, e.g., Carob/Caromax® (Zunft H J; et al., Carob pulp preparation for treatment of hypercholesterolemia, ADVANCES IN THERAPY (2001 September–October), 18(5), 230–6), Caromax is a carob-containing product from Nutrinova, Nutrition Specialties & Food Ingredients GmbH, Industriepark Höchst, 65926 Frankfurt/Main)). The combination with Caromax® can be effected in one preparation or by administering compounds of the formula I and Caromax® separately. In this connection, Caromax® can also be administered in the form of foodstuffs, such as in bakery products or muesli bars.

It will be understood that each suitable combination of the compounds according to the invention with one or more of the abovementioned compounds and, as desired, one or more further pharmacologically active substances, is regarded as coming within the protective scope of the present invention.

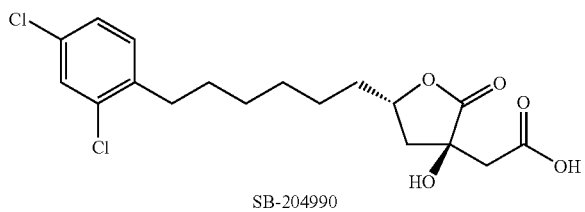
SB-204990

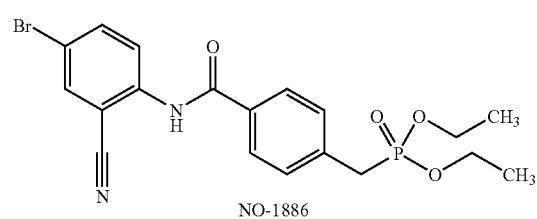
NO-1886

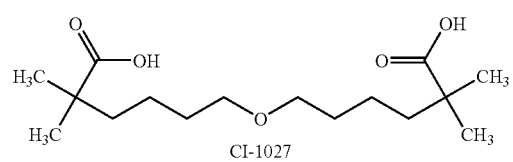
CI-1027

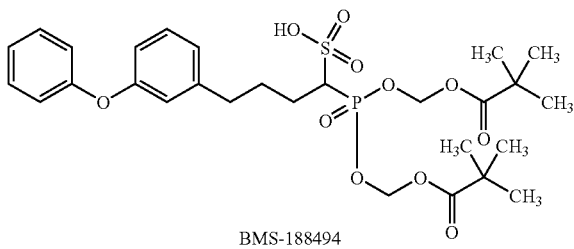
BMS-188494

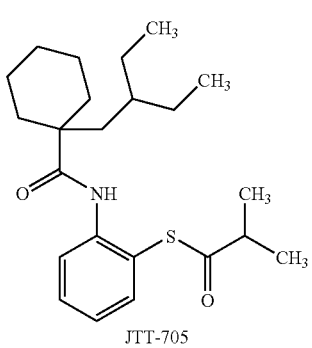
JTT-705

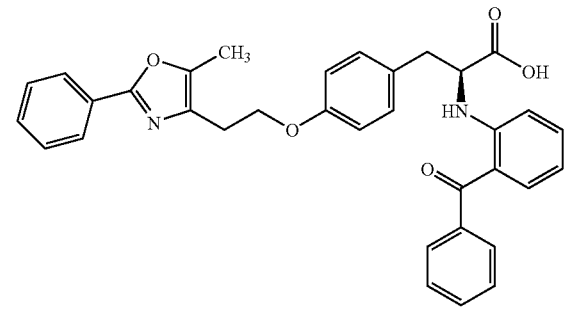
GI-262570

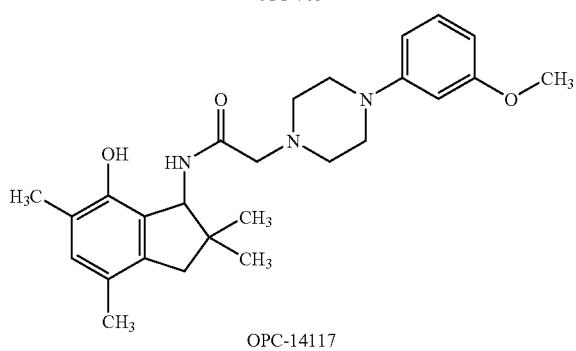
OPC-14117

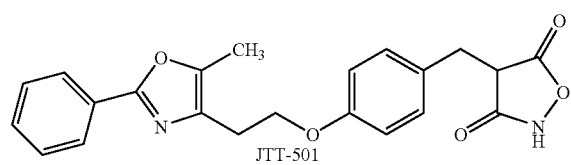
JTT-501

The examples which are adduced below serve to explain the invention without, however, limiting it.

TABLE 1

Compounds of the formula I

| Ex. | R7, R8, R9, R10 | R1 | R2 | R3 | R4 | R5 | R6 | Salt | MS* |
|---|---|---|---|---|---|---|---|---|---|
| 1 | 2-Cl, 4-Cl, H, H | H | H | $OCH_3$ | H | H | H | — | Ok |
| 2 | 2-Cl, H, H, H | H | H | $OCH_3$ | H | H | H | — | Ok |
| 3 | 2-Cl, 4-Cl, H, H | H | H | OH | H | H | H | — | Ok |
| 4 | 2-Cl, 4-Cl, H, H | H | H | F | H | H | H | — | Ok |
| 5 | 2-$CH_3$, H, H, H | H | H | Cl | H | H | H | — | Ok |
| 6 | 2-Cl, 5-Cl, H, H | H | H | Cl | H | H | H | — | Ok |
| 7 | 2-Cl, 5-Cl, H, H | H | H | Cl | H | H | H | TRIS | Ok |
| 8 | 2-$CH_3$, H, H, H | H | H | $OCH_3$ | H | H | H | — | Ok |
| 9 | 2-Cl, 5-Cl, H, H | H | H | $OCH_3$ | H | H | H | — | Ok |
| 10 | 3-Cl, 4-Cl, H, H | H | H | $OCH_3$ | H | H | H | — | Ok |
| 11 | 2-Cl, H, H, H | H | H | Cl | H | H | H | — | Ok |
| 12 | 2-Cl, 4-Cl, H, H | H | H | Cl | H | H | H | — | Ok |
| 13 | 2-Cl, 4-Cl, H, H | H | H | $OCH_2CH_3$ | H | H | H | — | Ok |
| 14 | 2-$CH_3$, 4-$CH_3$, H, H | H | H | $OCH_3$ | H | H | H | — | Ok |
| 15 | 2-F, 4-Cl, H, H | H | H | Cl | H | H | H | — | Ok |
| 16 | 2-F, 4-Cl, H, H | H | H | $OCH_3$ | H | H | H | — | Ok |
| 17 | 2-F, 4-F, H, H | H | H | Cl | H | H | H | — | Ok |
| 18 | 2-F, 4-F, H, H | H | H | $OCH_3$ | H | H | H | — | Ok |
| 19 | 2-Cl, 4-Cl, H, H | H | H | $OCH_2CH_2OH$ | H | H | H | — | Ok |
| 20 | 2-Cl, 4-Cl, H, H | H | H | $OCH_2CH_2CH_3$ | H | H | H | — | Ok |
| 21 | 2-Cl, 4-Cl, H, H | H | H | $OCH_2CH_2CH_2CH_3$ | H | H | H | — | Ok |
| 22 | 2-Cl, 4-Cl, H, H | H | H | $OCH_2CH_2OCH_3$ | H | H | H | — | Ok |
| 23 | 2-Cl, 4-Cl, H, H | H | H | O-phenyl | H | H | H | — | Ok |
| 24 | 2-Cl, 4-Cl, H, H | H | H | O-phenyl | H | H | H | TRIS | Ok |
| 25 | 2-Cl, 4-F, H, H | H | H | $CF_3$ | H | H | H | — | Ok |
| 26 | 2-Cl, 4-Cl, H, H | H | H | $CF_3$ | H | H | H | — | Ok |

*The information "MS is Ok" is understood as meaning that a mass spectrum or HPLC/MS was measured and the molar peak (molar mass + $H^{30}$) was detected in this spectrum Example 5 from EP 0 193 249 was synthesized as comparative example A. Example A has the structure:

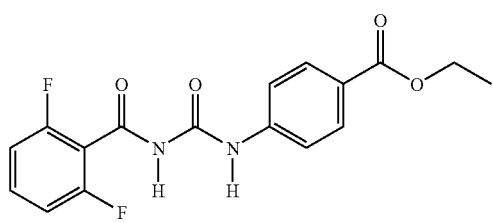

The compounds of the formula I are characterized by advantageous effects on sugar metabolism; in particular, they lower the blood sugar level and are suitable for treating type 2 diabetes. The compounds can therefore be used on their own or in combination with other blood sugar-lowering active compounds (antidiabetics).

The compounds of formula I are furthermore suitable for treating late damage in diabetes, such as nephropathy, retinopathy, neuropathy and cardiac infarction, myocardial infarction, peripheral arterial occlusion diseases, thromboses, arteriosclerosis, syndrome X, obesity, inflammations, immune diseases, autoimmune diseases, such as AIDS, asthma, osteoporosis, cancer, psoriasis, Alzheimer's disease, schizophrenia and infectious diseases.

The activity of the compounds was tested as follows:

Glycogen Phosphorylase a Activity Test

The effect of compounds on the activity of the active form of glycogen phosphorylase (GPa) was measured in the reverse direction by monitoring the synthesis of glycogen from glucose 1-phosphate by determining the release of inorganic phosphate. All the reactions were carried out as duplicate determinations in 96-well microtiter plates (Half Area Plates, Costar No. 3696), with the change in absorption due to the formation of the reaction product being measured, at the wavelength specified below, in a Multiscan Ascent Elisa Reader (Lab Systems, Finland). In order to measure the enzymic activity of GPa in the reverse direction, the conversion of glucose 1-phosphate into glycogen and inorganic phosphate was measured in accordance with the general method of Engers et al. (Engers HD, Shechosky S, Madsen NB, Can J Biochem 1970 July;48(7): 746–754) but with the following modifications: Human glycogen phosphorylase a (for example containing 0.76 mg of protein/ml (Aventis Pharma Deutschland GmbH), dissolved in buffer solution E (25 mM β-glycerophosphate, pH 7.0, 1 mM EDTA and 1 mM dithiothreitol), was diluted with buffer T (50 mM Hepes, pH 7.0, 100 mM KCl, 2.5 mM EDTA, 2.5 mM $MgCl_2.6H_2O$), and addition of 5 mg of glycogen/ml, to a concentration of 10 μg of protein/ml. Test substances were prepared as a 10 mM solution in DMSO and diluted down to 50 μM with buffer solution T. 10 μl of 37.5 mM glucose, dissolved in buffer solution T and 5 mg/ml of glycogen, and also 10 μl of a solution of human glycogen phosphorylase a (10 μg of protein/ml) and 20 μl of glucose 1-phosphate, 2.5 mM, were added to 10 ml of the solution. The basal value of the activity of the glycogen phosphorylase a in the absence of test substance was determined by adding 10 μl of buffer solution T (0.1% DMSO). The mixture was incubated at room temperature for 40 minutes and the inorganic phosphate which was released was measured using the general method of Drueckes et al. (Drueckes P, Schinzel R, Palm D, *Anal Biochem* 1955 Sep. 1;230(10):173–177) but with the following modifications: 50 μl of a stop solution of 7.3 mM ammonium molybdate, 10.9 mM zinc acetate, 3.6% ascorbic acid, 0.9% SDS are added to 50 μl of the enzyme mixture. After 60 minutes of incubation at 45° C., the absorption was measured at 820 nm. In order to determine the background absorption, the stop solution was added immediately after adding the glucose 1-phosphate solution in a separate assay. This test was carried out using a 10 μM concentration of the test substance in order to determine the respective inhibition of glycogen phosphorylase a by the test substance in vitro.

TABLE 2

Biological activity

| Ex. | % inhibition at 10 μM |
|---|---|
| 1 | 95 |
| 2 | 75 |
| 3 | 74 |
| 4 | 75 |
| 5 | 46 |
| 6 | 57 |
| 7 | 54 |
| 8 | 77 |
| 9 | 81 |
| 10 | 41 |
| 11 | 49 |
| 12 | 83 |
| 13 | 86 |
| 14 | 57 |
| 15 | 61 |
| 16 | 48 |
| 17 | 52 |
| 18 | 69 |
| 19 | 90 |
| 20 | 62 |
| 21 | 64 |
| 22 | 72 |
| 23 | 55 |
| 24 | 65 |
| 25 | 49 |
| 26 | 44 |

Comparative Example A exhibits 3% inhibition at 10 μM.

It can be seen from the table that the compounds of the formula I inhibit the activity of glycogen phosphorylase a and are therefore well suited for lowering the blood sugar level. In particular, the compounds of formula I exhibit an effect which is from 14- to 32-fold higher than that of comparative example A.

The preparation of one example is described in detail below; The remaining compounds of formula I were obtained in an analogous manner:

Experimental section:

EXAMPLE 1 a) 2,4-Dichlorobenzoyl isocyanate 2,4-Dichlorobenzamide was dissolved in dichloromethane, after which 1.5 eq. of oxalyl chloride were added and the mixture was heated to reflux for 16 hours. The reaction mixture was then concentrated under high vacuum and reacted in step b without any further purification.

b) 3-[3-(2,4-Dichlorobenzoyl)ureido]-4-methoxybenzoic acid 20 g (120 mmol) of 3-amino-4-methoxybenzoic acid were made to react with 36 g (168 mmol) of 2,4-dichlorobenzoyl isocyanate from step a in 400 ml of acetonitrile and left to react therewith at reflux for 2 hours. After the mixture has cooled down to room temperature, the precipitate is filtered off with suction, washed twice with in each case 20 ml of acetonitrile, sucked dry and dried under high vacuum. 44 g (96%) of the desired product are obtained.

m.p.: 290° C.

What is claimed is:
1. A compound of the formula I,

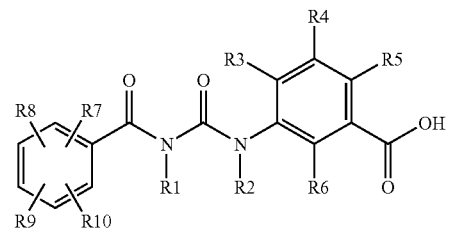

in which
R7, R8, R9 and R10 are, independent of each other, H, F, Cl, Br, OH, NO$_2$, CN, O—(C$_1$–C$_6$)-alkyl, O—(C$_2$–C$_6$)-alkenyl, O—(C$_2$–C$_6$)alkynyl, O—SO$_2$—(C$_1$–C$_4$)alkyl, (C$_1$–C$_6$)-alkyl, (C$_2$–C$_6$)-alkenyl or (C$_2$–C$_6$)-alkynyl, wherein alkyl, alkenyl and alkynyl can be substituted, once or more than once, by F, Cl or Br;
R1 and R2 are, independent of each other, H, (C$_1$–C$_6$)-alkyl, wherein alkyl cat be substituted by OH, O—(C$_1$–C$_4$)-alkyl, NH$_2$, NH(C$_1$–C$_4$)-alkyl or N[(C$_1$–C$_6$) alkyl]$_2$, O—(C$_1$–C$_6$)-alkyl, CO-(C$_1$–C$_6$)-alkyl, COO-(C$_1$–C$_6$)-alkyl, (C$_1$–C$_6$)-alkylene-COOH or (C$_1$–C$_6$)-alkylene-COO—(C$_1$–C$_6$)-alkyl;
R3 is H, F, Cl, Br, NO$_2$, CN, O—R11, unsubstituted O-phenyl, S—R11, COOR11, N(R12)(R13), (C$_1$–C$_6$)-alkyl, (C$_2$–C$_6$)-alkenyl, (C$_2$–C$_6$)-alkynyl, (C$_3$–C$_7$)-cycloalkyl or (C$_3$–C$_7$)-cycloalkyl-(C$_1$–C$_4$)-alkylene, wherein alkyl, cycloalkyl and alkynyl can be substituted, once or more than once, by F, Cl, Br, OR11, COOR11 or N(R16)(R17);
R4 is H, F, Cl, Br, NO$_2$, CN, O—R11, O-phenyl, S—R11, COOR11, N(R12)(R13), (C$_1$–C$_6$)-alkyl, (C$_2$–C$_6$)-alkenyl, (C$_2$–C$_6$)-alkynyl, (C$_3$–C$_7$)-cycloalkyl or (C$_3$–C$_7$)-cycloalkyl-(C$_1$–C$_4$)-alkylene, wherein alkyl, cycloalkyl and alkynyl can be substituted, once or more than once, by F, Cl, Br, OR11, COOR11 or N(R16)(R17);

R5 is H, F, Cl, Br, $NO_2$, CN, O—R11, O-phenyl, S—R11, COOR11, N(R12)(R13), $(C_1-C_6)$-alkyl, $(C_2-C_6)$-alkenyl, $(C_2-C_6)$-alkynyl, $(C_3-C_7)$-cycloalkyl or $(C_3-C_7)$-cycloalkyl-$(C_1-C_4)$-alkylene, wherein alkyl, cycloalkyl and alkynyl can be substituted, once or more than once, by F, Cl, Br, OR11, COOR11 or N(R16)(R17);

R6 is H, F, Cl, Br, $NO_2$, CN, O—R11, unsubstituted O-phenyl, S—R11, COOR11, N(R12)(R13), $(C_1-C_6)$-alkyl, $(C_2-C_6)$-alkenyl, $(C_2-C_6)$-alkynyl, $(C_3-C_7)$-cycloalkyl or $(C_3-C_7)$-cycloalkyl-$(C_1-C_4)$-alkylene, wherein alkyl, cycloalkyl and alkynyl can be substituted, once or more than once, by F, Cl, Br, OR11, COOR11 or N(R16)(R17);

R11 is H, $(C_1-C_8)$alkyl, $(C_2-C_8)$-alkenyl or $(C_2-C_8)$-alkynyl, wherein alkyl, alkenyl and alkynyl can be substituted, once or more than once, by F, Cl, Br, OH or O—$(C_1-C_4)$-alkyl;

R12 and R13 are, independent of each other, H, $(C_1-C_8)$ alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring can be substituted, up to two times, by F, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or R12 and R13 form, together with the nitrogen atom to which they are bonded, a 3–7-membered, saturated heterocyclic ring which can contain up to 2 further heteroatoms from the group N, O or S and wherein the heterocyclic ring can be substituted, up to four times, by F, Cl, Br, OH, Oxo (i.e. O═), $(C_1-C_4)$-alkyl or N(R14)(R15);

R14 and R15 are, independent of each other, H $(C_1-C_8)$-alkynyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_1-C_4)$-alkenyl, phenyl or $SO_2$-phenyl, wherein the phenyl ring can be substituted, up to two times, by F, Cl, CN, OH, $(C_1-C_6)$-alkyl, O—$(C_1-C_6)$-alkyl, $CF_3$, $OCF_3$, COOH, COO$(C_1-C_6)$-alkyl or $CONH_2$;

R16 and R17 are, independent of each other, H, $(C_1-C_8)$-alkyl, $(C_2-C_8)$-alkenyl, $(C_2-C_8)$ alkynyl, $(C_3-C_7)$-cycloalkyl, $(C_3-C_7)$-cycloalkyl-$(C_1$—$)$-alkylene, COO—$(C_1-C_4)$-alkyl, COO—$(C_2-C_4)$— alkenyl, phenyl or $SO_2$-phenyl, wherein the phenyl ring can be substituted, up to two times, by F, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or R16 and R17 form, together with the nitrogen atom to which they are bonded, a 3–7-membered, saturated heterocyclic ring which can contain up to 2 further heteroatoms from the group N, O or S and wherein the heterocyclic ring can be substituted, up to four times, by F, Cl, Br, OH, Oxo (i.e. O═), $(C_1-C_4)$-alkyl or N(R14)(R15);

and a pharmaceutically acceptable salt thereof.

2. A compound of formula I as claimed in claim 1 wherein

R7, R8, R9 and R10 are, independent of each other, H, F, Cl, Br, OH, $NO_2$, CN, $(C_1-C_6)$-alkyl or O—$(C_1-C_6)$-alkyl;

R1 and R2 are H;

R3 is H, F, Cl, Br, $NO_2$, CN, O—R11, unsubstituted O-phenyl, S—R11, COOR11, N(12)(R13), $(C_1-C_6)$-alkyl, $(C_2-C_6)$-alkenyl, $(C_2-C_6)$-alkynyl, $(C_3-C_7)$-cycloalkyl or $(C_3-C_7)$-cycloalkyl-$(C_1-C_4)$-alkylene, wherein alkyl, cycloalkyl and alkynyl can be substituted, once or more than once, by F, Cl, Br, OR11, COOR11 or N(R16)(R17);

R4 is H, F, Cl, Br, $NO_2$, CN, O—R11, O-phenyl, S—R11, COOR11, N(R12)(R13), $(C_1-C_6)$-alkyl, $(C_2-C_6)$-alkenyl, $(C_2-C_6)$-alkynyl, $(C_3-C_7)$-cycloalkyl or $(C_3-C_7)$-cycloalkyl-$(C_1-C_4)$-alkylene, wherein alkyl, cycloalkyl and alkynyl can be substituted, once or more than once, by F, Cl, Br, OR11, COOR11 or N(R16)(R17);

R5 is H, F, Cl, Br, $NO_2$, CN, O—R11, O-phenyl, S—R11, COOR11, N(R12)(R13), $(C_1-C_6)$-alkyl, $(C_2-C_6)$-alkenyl, $(C_2-C_6)$-alkenyl, $(C_3-C_7)$-cycloalkyl or $(C_3-C_7)$-cycloalkyl-$(C_1-C_4)$-alkylene, wherein alkyl, cycloalkyl and alkynyl can be substituted, once or more than once, by F, Cl, Br, OR11, COOR11 or N(R16)(R17);

R6 is H, F, Cl, Br, $NO_2$, CN, O—R11, unsubstituted O-phenyl, S—R11, COOR11, N(R12)(R13), $(C_1-C_6)$-alkyl, $(C_2-C_6)$-alkenyl, $(C_2-C_6)$-alkynyl, $(C_3-C_7)$-cycloalkyl or $(C_3-C_7)$-cycloalkyl-$(C_1-C_4)$-alkylene, wherein alkyl, cycloalkyl and alkynyl can be substituted, once or more than once, by F, Cl, Br, OR11, COOR11 or N(R16)(R17);

R11 is H, $(C_1-C_8)$-alkyl, $(C_1-C_8)$-alkylene-O—$(C_1-C_8)$-alkyl or $(C_1-C_8)$-alkyl-OH, wherein alkyl can be substituted, once or more than once, by F;

R12 and R13 are, independent of each other, H or $(C_1-C_8)$-alkyl;

R14 and R15 are, independent of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring can be substituted, up to two times, by, F, Cl, CN, OH, $(C_1-C_6)$-alkyl, O—$(C_1-C_6)$-alkyl, $CF_3$, $OCF_3$, COOH, COO$(C_1-C_6)$-alkyl or $CONH_2$;

R16 and R17 are, independent of each other, H, $(C_1-C_8)$-alkyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$alkyl, COO—$(C_2-C_4)$-alkenyl, phenyl or $SO_2$-phenyl, wherein the phenyl ring can be substituted, up to two times, by F, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or R16 and R17 form, together with the nitrogen atom to which they are bonded, a 3–7-membered, saturated heterocyclic ring which can contain up to 2 further heteroatoms from the group N, O or S and wherein the heterocyclic ring can be substituted, up to four times, by F, Cl, Br, OH, Oxo (i.e. O═)$(C_1-C_4)$-alkyl or N(R14)(R15);

and a pharmaceutically acceptable salt thereof.

3. A compound of formula I as claimed in claim 1 or 2, wherein

R7, R8, R9 and R10 are independently H, F, Cl or $CH_3$;

R1, R2, R4, R5 and R6 are H;

R3 is F, Cl, $CF_3$, O—R11 or unsubstituted O-phenyl;

R11 is H, $(C_1-C_8)$-alkyl, $(C_1-C_8)$-alkylene-O—$(C_1-C_8)$-alkyl or $(C_1-C_8)$-alkyl-OH; and a pharmaceutically acceptable salt thereof.

4. A pharmaceutical which comprises one or more of the compounds as claimed in claim 1 and a pharmaceutically acceptable carrier.

5. A pharmaceutical which comprises one or more of the compounds as claimed in claim 1 and one or more blood sugar-lowering active compounds and a pharmaceutically acceptable carrier.

6. A method of treating type 2 diabetes in a patient in need thereof, comprising administering to said patient a pharmaceutically effective amount of a compound of claim 1.

7. A method of lowering blood sugar level to normal level in a human diabetes patient, wherein said blood sugar level being above normal blood sugar level, comprising administering to said patient a pharmaceutically effective amount of a compound of claim 1.

8. A method of treating type 2 diabetes in a patient in need thereof, comprising administering to said patient a pharmaceutically effective amount of a compound of claim 1 in combination with at least one further blood sugar-lowering active compound.

9. A method of lowering blood sugar level to normal level in a human diabetes patient, wherein said blood sugar level being above normal blood sugar level, comprising administering to said patient a pharmaceutically effective amount of a compound of claim 1 in combination with at least one further blood sugar-lowering active compound.

10. A process for producing a pharmaceutical which comprises one or more of the compounds as claimed in claim 1, which comprises mixing the active compound with a pharmaceutically suitable excipient and bringing this mixture into a form which is suitable for administration.

* * * * *